United States Patent [19]
Banzi et al.

[11] Patent Number: 5,917,072
[45] Date of Patent: Jun. 29, 1999

[54] CATALYSTS FOR THE POLYMERIZATION OF ALPHA-OLEFINS

[75] Inventors: Viviano Banzi, Vigarano Mainarda; Paolo Biagini, Trecate; Roberto Santi; Giampiero Borsotti, both of Novara; Gabriele Lugli, S. Donato Milanese, all of Italy

[73] Assignee: Enichem S.p.A., Milano, Italy

[21] Appl. No.: 08/761,140

[22] Filed: Dec. 6, 1996

[30] Foreign Application Priority Data

Dec. 22, 1995 [IT] Italy .................................. MI95A2731

[51] Int. Cl.$^6$ ................ C07F 17/00; C07F 7/00

[52] U.S. Cl. .............. 556/53; 556/54; 502/103; 502/117; 526/160; 526/943

[58] Field of Search .............. 556/53, 54; 526/943, 526/160; 502/103, 117

[56] References Cited

U.S. PATENT DOCUMENTS

| | | | |
|---|---|---|---|
| 5,276,208 | 1/1994 | Winter et al. | 556/53 |
| 5,510,502 | 4/1996 | Sugano et al. | 556/11 |

FOREIGN PATENT DOCUMENTS

| | | |
|---|---|---|
| 0 490 256 | 6/1992 | European Pat. Off. . |
| 0 693 506 | 1/1996 | European Pat. Off. . |
| 0 697 418 | 2/1996 | European Pat. Off. . |
| WO/96 02580 | 2/1996 | WIPO . |

OTHER PUBLICATIONS

Krueger et al., J. Organomet. Chem., vol. 452, No. 1–2, pp. 79–86, 1993.

Chemical Abstracts, vol. 124, No. 4, Jan. 22, 1996, AN–30612x, T. Sunaga, et al., "Metallocene Compounds and Polymerization of Olefins Therewith", JP–A–07 173 208.

Chemical Abstracts, vol. 124, No. 5, Jan. 29, 1996, AN–56154z, L.A. Paquette, et al., "Catalytic Enantioselective Hydrogenation of 1,1–Disubstituted Alkenes with Optically Active Titanocene and Zirconocene Complexes Containing Either Identical or Different Ligands".

Journal of Organometallic Chemistry, vol. 472, pp. 205–213, 1994, H.W. Bosch, et al., "Synthese Bicyclicsher Pentaalkylcyclopentadiene und Ihrer Metallkomplexe. Kristallstruktur Von Bis (1,2,3–Trimethylbicyclo (4.3.0) Nonadienyl)Eisen".

Journal of Organometallic Chemistry, vol. 378, pp. 153–161, 1989, P. Burger, et al., "Ansa–Metallocene Derivatives. XVIII. Chiral Titanocene Derivatives Accessible from Substituted Dihydropentalene and Azulene Precursors".

Journal of Organometallic Chemistry, vol. 465, pp. 175–179, 1994, R.L. Halterman, et al., "Electronic Effects of Bis(2–Aryl–4,5,6,7–Tetrahydroindenyl)Titanocene Dichlorides on the Catalytic Epoxidation of Trans–3–Hexene".

*Primary Examiner*—Porfirio Nazario-Gonzalez
*Attorney, Agent, or Firm*—Oblon, Spivak, McClelland, Maier & Neustadt, P.C.

[57] ABSTRACT

A description follows of catalysts of the metallocene type which can be used in the (co)polymerization of alpha-olefins, particularly in the preparation of elastomeric copolymers of ethylene.

9 Claims, No Drawings

CATALYSTS FOR THE POLYMERIZATION OF ALPHA-OLEFINS

The present invention relates to new catalysts of the metallocene type and to the process for the production of (co)polymers of alpha-olefins, particularly elastomeric copolymers of ethylene α-olefins, particularly ethylene-propylene, which uses these catalysts.

Elastomeric copolymers based on olefins can be prepared by the polymerization of ethylene and an α-olefin, possibly in the presence of a diene. The most common elastomers based on olefins are elastomeric copolymers ethylene-propylene (EP elastomers) and ethylene, propylene, diene terpolymers (EPDM).

For the above copolymerizations complexes of zirconium or titanium are being continually developed with ligands of the bis-indenyl, bis-fluorenyl or mixed type, such as fluorenyl cyclopentadienyl ligands (P. C. Mohring, N. J. Coville, J.Organomet. Chem. 479, 1, 1994).

These catalysts however have the disadvantage of not always producing copolymers with an acceptable viscosity from an applicative point of view, particularly in the preparation of elastomeric ethylene-propylene copolymers with a propylene content of between 40 and 65% by weight, a composition range which gives the best results in terms of elastomeric properties.

It is also known that in the preparation of EP or EPDM copolymers, the copolymerization is often carried out in the presence of hydrogen as molecular weight regulator.

The use of hydrogen however sometimes creates considerable difficulties due to the high sensitivity to hydrogen of the catalytic system based on metallocenes. As a result the quantities of hydrogen suitable for regulating the molecular weight are too small to be conveniently distributed.

New complexes of Zirconium have now been found which overcome the above drawbacks. The above catalysts are also active in the (co)polymerization of alpha-olefins.

In accordance with this, the present invention relates to a catalytic component for the (co)polymerization of alpha-olefins characterized in that it comprises one or more compounds having general formula (I)

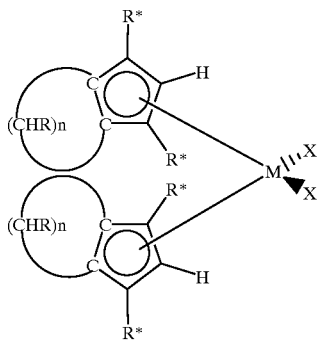

(I)

wherein "X" is selected from halogen, hydride, hydrocarbyl radical, alkoxide, dialkylamide, preferably from halogen, hydride, hydrocarbyl radical; even more preferably is chlorine; "n" is an integer between 2 and 18, and is preferably selected from 3, 5, 6, 10;

R and R* are selected from H, alkyl radicals having from 1 to 5 carbon atoms, cycloalkyl radicals having from 5 to 8 carbon atoms, aryl and alkyl aryl radicals having from 6 to 8 carbon atoms, aralkyl radicals having from 7 to 9 carbon atoms, "M" is Zirconium, with the proviso that, referring to general formula (II), the number of R different from H is not higher than 2;

at least one of two R* is H, preferably the two R* are selected from H and C1–C3 alkyl radical; excluding the compound having n=4, R=R*=R*=H. The compounds having general formula (I) can be prepared starting from cyclopentadienyl derivatives having general formula (II) described in the copending patent application filed by the same applicant IT-A-MI95 02707.

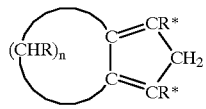

(II)

With respect to the meanings of R and R*, typical examples of $C_1$ to $C_5$ alkyl radicals are methyl, ethyl, n-propyl, iso-propyl, n-butyl, iso-butyl, ter-butyl, n-pentyl, iso-pentyl, neo-pentyl.

Typical examples of cycloalkyl radicals having from 5 to 8 carbon atoms are cyclopentyl, cyclohexyl, methylcyclopentyl, methylcyclohexyl.

Typical examples of aryl and alkyl aryl radicals having from 6 to 8 carbon atoms are phenyl, methylphenyl, ethylphenyl, dimethylphenyl.

In a preferred form of embodiment R and R* are selected from H and $C_1$ to $C_3$ alkyl radicals. In an even more preferred form of embodiment, n is selected from 3,5,6,10, R is H, R* are selected from H and $C_1$ to $C_3$ alkyl radicals.

Non-limiting examples of compounds having general formula (I) are:

(1) bis-(4,5,6-trihydro-pentalenyl)zirconium dichloride;

(2) bis-(1-methyl-4,5,6-trihydro-pentalenyl)zirconium dichloride;

(3) bis-(4-methyl-4,5,6-trihydro-pentalenyl) zirconium dichloride;

(4) bis-(1,4-dimethyl-4,5,6-trihydro-pentalenyl) zirconium dichloride;

(5) bis-(5-methyl-4,5,6-trihydro-pentalenyl) zirconium dichloride;

(6) bis-(1,5-dimethyl-4,5,6-trihydro-pentalenyl) zirconium dichloride;

(7) bis-(5-phenyl-4,5,6,7-tetrahydro-indenyl)zirconium dichloride;

(8) bis-(4,5,6,7,8-pentahydro-azulenyl)zirconium dichloride;

(9) bis-(1-methyl-4,5,6,7,8-pentahydro-azulenyl) zirconium dichloride;

(10) bis-(4,5,6,7,8,9-hexahydro-cyclopentacyclooctenyl) zirconium dichloride;

(11) bis-(1-methyl-4,5,6,7,8,9-hexahydro-cyclopentacyclooctenyl)zirconium dichloride;

(12) bis-(4,5,6,7,8,9,10,11-octahydro-cyclopentacyclodecenyl) zirconium dichloride;

(13) bis-(1-methyl-4,5,6,7,8,9,10,11-octahydrocyclopentacyclodecenyl)zirconium dichloride;

(14) bis-(4,5,6,7,8,9,10,11,12,13-decahydro-cyclopentacyclododecenyl)zirconium dichloride;

(15) bis-(1-methyl-4,5,6,7,8,9,10,11,12,13-decahydrocyclopentacyclododecenyl)zirconium dichloride;

(16) bis-(5,6-diphenyl-4,5,6,7-tetrahydro-indenyl) zirconium dichloride;

(17) bis-(1-phenyl-4,5,6,7,8-pentahydro-azulenyl) zirconium dichloride;

(18) bis-(1-phenyl-4,5,6,7,8,9-hexahydro-cyclopentacyclooctenyl)zirconium dichloride;

(19) bis-(1-phenyl-4,5,6,7,8,9,10,11,12,13-decahydrocyclopentacyclododecenyl)zirconium dichloride;

Other examples are those in which, again with reference to compounds 1 to 19, the chlorides are substituted with methyls, phenyls, methoxides, phenoxides.

A typical example, which is illustrative but not limiting, for the preparation of the compounds having general formula (I) consists in reacting the compound with general formula (II), which we will call in short HR$^b$, with ZrCl$_4$ according to the following scheme:

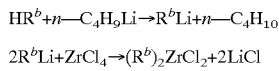

2R$^b$Li+ZrCl$_4$→(R$^b$)$_2$ZrCl$_2$+2LiCl

A further object of the present invention relates to a process for the homo and copolymerization of C$_2$–C$_{20}$, particularly C$_2$–C$_{10}$ alpha-olefins, which uses a catalytic system which comprises the compound having general formula (I).

In the (co)polymerization of alpha-olefins, the catalytic system also comprises, in addition to the metallocene having general formula (I), another component (which we will call co-catalyst) selected from alumoxane and compounds having general formula (III) (Ra)$_x$NH$_{4-x}$B(Rd)$_4$, or (IV) (Ra)$_3$PHB(Rd)$_4$, or (V) B(Rd)$_3$, which by reaction with a metallocene having general formula (I) are capable of generating catalytic systems of ionic nature. In the above compounds having general formula (III), (IV) or (V), the Ra groups, the same or different, are monofunctional alkyl or aryl radicals, whereas Rd, the same or different, are monofunctional aryl radicals, preferably partially or totally fluorinated, even more preferably totally fluorinated. When compounds having general formula (III), (IV) or (V) are used as co-catalysts, the catalytic system will basically consist of reaction products of one or more metallocenes having general formula (I), in which X is equal to H or a hydrocarbyl radical, with any one of the compounds having general formula (III), (IV) or (V), or a mixture thereof, as described in EP-A-277,004, the molar ratio between the compound having general formula (III), (IV) or (V) and the metallocene having general formula (I) being between 0.1 and 10, preferably between 0.5 and 3, even more preferably between 0.7 and 2.

When X is different from H or hydrocarbyl radical, the catalytic system consists of one or more metallocenes having general formula (I), an alkylating compound (VI) selected from aluminum trialkyl, magnesium dialkyl or lithium alkyl or other alkylating agents well known to experts in the field, and any of the compounds having general formula (III), (IV) or (V), or a mixture thereof, as described in EP-A-612769.

The formation procedure of the catalytic system involves the premixing of the metallocene compound having general formula (I) with a suitable alkylating agent (VI) in aliphatic or aromatic hydrocarbon solvents, or their mixtures, at a temperature of between –20° to +100° C., preferably between 0° C. and 60° C. and more preferably between +20° C. and +50° C., for a time varying from 1 minute to 24 hours, preferably from 2 minutes to 12 hours, even more preferably from 5 minutes to 2 hours. The mixture is then put in contact with a compound having general formula (III), (IV) or (V), at the above temperature for a time of between 1 minute and 2 hours, preferably between 2 minutes and 30 minutes, and is subsequently fed into the polymerization reactor.

The molar ratio between the alkylating compound (VI) and the compound having general formula (I) can vary from 1 to 1000, preferably from 10 to 500, even more preferably from 30 to 300.

The molar ratio between the compound having general formula (III), (IV) or (V) and the metallocene (I) can vary from 0.1 to 10, preferably from 0.5 to 3, even more preferably from 0.7 to 2.

As regards the alumoxane, this is a compound of aluminum which, in its linear form, has the general formula (VII)

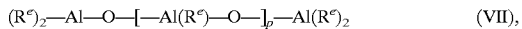

whereas in its cyclic form it has the general formula (VIII)

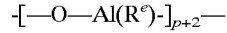

wherein R$^e$, the same or different, are selected from C$_1$–C$_6$ alkyl radicals, C$_6$–C$_{18}$ aryl radicals or H, "p" is an integer between 2 and 50, preferably between 10 and 35. The various R$^e$ are preferably the same as each other and are selected from methyl, isobutyl, phenyl or benzyl, preferably methyl.

When the various R$^e$ are different, they are preferably methyl and hydrogen or alternatively methyl and isobutyl, the hydrogen or isobutyl being preferably present, as the number of R$^e$ radicals, in between 0.1 and 40% by weight.

The alumoxane can be prepared according to various methods known to experts in the field. One of the methods, for example, comprises the reaction of an aluminium-hydrocarbon compound and/or an aluminium-hydroaluminium with water (gaseous, solid, liquid or linked, for example, as crystallization water) in an inert solvent, for example, toluene. For the preparation of an alumoxane having different R$^e$ alkyl groups, two different aluminium-trialkyls (AlR$_3$+AlR'$_3$), are reacted with water (see S. Pasynkiewicz, Polyhedron 9 (1990) 429–430 and EP-A-302 424).

The exact structure of the alumoxane is not known. It is possible to preactivate the metallocene with the alumoxane before its use in the polymerization phase. This considerably increases the polymerization activity and improves the morphology of the particles. The above preactivation is preferably carried out in a solvent, by dissolving the metallocene in a solution of an inert hydrocarbon, preferably aliphatic or aromatic, even more preferably in toluene. The concentration of the alumoxane in the solution is in the range of 1% by weight up to the saturation value, preferably from 5 to 30% by weight with respect to the total weight of the solution. The metallocene can be used in the same concentration but is preferably used in a quantity of between 10$^{-4}$ and 1 mole per mole of alumoxane. The preactivation time is between 5 minutes and 60 hours, preferably between 5 and 60 minutes. The temperature is between –78° C. and 100° C., preferably between 0° and 70° C.

The catalytic system of the present invention (catalyst having general formula (I) and co-catalyst) can be prepared by putting the catalyst in contact with the co-catalyst in the presence of or without the monomer to be polymerized, inside or outside the reaction reactor.

The quantities of catalyst and co-catalyst are not particularly limited. For example, in the case of polymerization in a solvent, the quantity of catalyst is preferably in the range of $10^{-7}$ and $10^2$ mmoles/liter, even more preferably from $10^{-4}$ to 1 mmole/liter, in terms of transition metal M. When alumoxane is used, the molar ratio between the Aluminum and the transition metal M is preferably higher than 10 and lower than 10,000.

As well as the catalyst and co-catalyst, the catalytic system can contain a third optional component, usually one or more substances having active hydrogen atoms, such as water, alkanols (for example methanol, ethanol, butanol), or electron-donor compounds, such as ethers, esters, amines, compounds containing alkoxide groups such as phenylborates, dimethylmethoxyaluminium, phenyl phosphate, tetraethoxysilane, diphenyldimethoxysilane.

The catalyst and co-catalyst can be introduced separately into the reaction reactor or after being previously in contact with each other. In the latter case the contact can be carried out in the presence of a monomer which is then to be polymerized, thus effecting the so-called "preliminary polymerization".

To return to the copolymerization process, it is convenient to remove catalyst poisons which are possibly present in the monomers, particularly in propylene. In this case purification can be carried out with an aluminiumalkyl, for example $AlMe_3$, $AlEt_3$, $Al(iso-Bu)_3$. This purification can be carried out in the polymerization system or, alternatively, before polymerization by putting the propylene in contact with the Aluminum alkyl and subsequently separating it.

The catalytic system of the present invention can be applied to polymerization in the slurry phase (where a disperser is used, for example, propane or butane), to polymerization basically carried out without a solvent (such as polymerization without a solvent in a liquid phase and polymerization in a gas phase), and polymerization in solution. The catalyst of the invention can obviously be applied to polymerization in continuous or batch.

When the polymerization is carried out in a solvent, aliphatic and aromatic hydrocarbons can be conveniently used as diluents, either alone or mixed with each other.

The catalytic component having general formula (I) can be supported on inert carriers. Techniques suitable for supporting metallocene components on porous solids, for example silica and alumina, possibly in the presence of the co-catalyst, are well-known in literature. The catalytic system thus supported can be used as such or prepolymerized with alpha-olefin monomers. Supporting enables heterogeneous catalytic components to be obtained with a specific morphology and particle size, particularly suitable for polymerization processes in gas phase.

The polymerization temperature is approximately in the range of $-78°$ C. to $200°$ C., preferably from $-20°$ to $100°$ C. There are no particular limitations in the olefin pressure in the reaction system, even if the pressure is preferably within the range from atmospheric pressure to 50 kg/cm$^2$ G. In the polymerization process, the molecular weight can be controlled with any known method, for example by suitably selecting the polymerization temperature and pressure or by introducing hydrogen.

Olefins which can be polymerized with the process of the present invention are alpha-olefins (comprising ethylene) having from 2 to 20 carbon atoms, preferably from 2 to 10 carbon atoms. Typical examples of alpha-olefins which can be (co)polymerized with the process of the present invention are ethylene, propylene, 1-butene, 4-methyl-1-pentene, 1-hexene, 1-octene, 1-decene, 1-dodecene, 1-tetradecene, 1-hexadecene, 1-octadecene, 1-eicosene.

A further object of the present invention relates to a process for the preparation of elastomeric ethylene / α-olefin copolymers or elastomeric ethylene / α-olefin / diene terpolymers, preferably ethylene-propylene(EPM) or ethylene-propylene-diene (EPDM) with a propylene content of between 15 and 75% by weight, preferably between 25 and 70% by weight, even more preferably between 40 and 60% by weight, which comprises the following steps:

1) an α-olefin and the possible diene are fed into the polymerization reactor, preferably diluted with a $C_3$–$C_5$ low-boiling hydrocarbon, preferably propane, at such a pressure as to allow the use of this α-olefin in a liquefied form;
2) ethylene is added to the mixture obtained in step (1) in a quantity which is sufficient to maintain the desired ratio ethylene/-olefin in the liquid phase;
3) the catalytic system is added comprising one or more metallocenes and one or more co-catalysts selected from alumoxane and compounds having general formula (III) $(Ra)_xNH_{4-x}B(Rd)_4$ or having general formula (IV) $(Ra)_3PHB(Rd)_4$ or general formula (V) $B(Rd)_3$, possibly in the presence of an alkylating compound (VI);
4) the mixture obtained in step (3) is reacted for a time which is sufficient to allow the polymerization of the ethylene-alpha-olefin and possible diene system to give an EP(D)M having a Mooney viscosity ($ML_{1+4}$ at $100°$ C.) greater than 25, characterized in that the catalytic system comprises a metallocene selected from those having general formula (I)

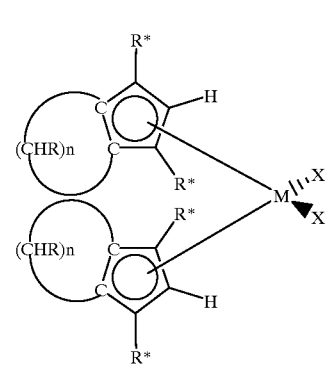

(I)

wherein each "X" is independently selected from halogen, hydride, hydrocarbyl radical, alkoxide, dialkylamide, and is preferably selected from halogen, hydride, hydrocarbyl radical;

"n" is an integer between 2 and 18, and is preferably selected from 3,4,5,6,10;

R and R* are selected from H, alkyl radicals having from 1 to 5 carbon atoms, cycloalkyl radicals having from 5 to 8 carbon atoms, aryl and alkyl aryl radicals having from 6 to 8 carbon atoms, aralkyl radicals having from 7 to 9 carbon atoms, "M" is Zirconium, with the proviso that, referring to general formula (II),
the number of R different from H is not higher than 2;
at least one of two R* is H, preferably the two R are selected from H and $CH_3$;
excluding the compound having n=4, R=R*=H.

In a preferred form of embodiment, R and R* are selected from H and $C_1$ to $C_3$ alkyl radicals.

In an even more preferred form of embodiment, n is selected from 3,5,6,10, R is H, R* are selected from H and $C_1$ to $C_3$ alkyl radicals.

The alpha-olefins which can be used in the production of copolymers with ethylene are those described above. Typical examples of dienes which can be used for the preparation of EPDM are 5-ethylidene-2-norbornene (ENB), 1,4-hexadiene, dicyclopentadiene; the diene is preferably 5-ethylidene-2-norbornene.

When EPDM are prepared, the diene content in the polymer is less than 15% by weight, preferably from 2 to 10%, the propylene content being that specified above.

The process for the production of EP(D)M is carried out by the polymerization in a slurry phase of ethylene, alpha-olefin, preferably propylene, and the possible diene, optionally diluted with a low-boiling form $C_3$ to $C_5$ hydrocarbon, preferably propane.

A catalytic system is suspended in this mixture, consisting of the metallocene having general formula (I) and the co-catalyst selected from MAO and compounds having general formula (III), (IV) and (V), and optionally the alkylating compound (VI). This catalytic system is present in such a quantity as to provide a sufficient quantity of polymer containing the optional diene.

The concentration of the optional diene in the reactor, as a volume percentage, is between 0.05 and 10, preferably between 0.2 and 4%.

The ethylene is fed to the reactor at a pressure higher than the pressure inside the reactor. The ethylene content of the polymer is determined from the ratio between the partial ethylene pressure and the total pressure in the polymerization reactor. This partial ethylene pressure is generally maintained at between 0.5 and 50 bars, more preferably between 1 and 15 bars. The temperature of the reactor is kept at between $-10°$ and $90°$ C., more preferably between $20°$ and $60°$ C. Under these operating conditions, ethylene, alpha-olefin and the optional diene polymerize to give an EP(D)M elastomer.

The polymerization can be carried out with a slurry process batchwise or preferably in continuous with a constant feeding of the mixture of monomers, possibly diluted with the low-boiling hydrocarbon, and the catalytic system.

Without any limitations to the scope of the present invention, a procedure for carrying out the process of the present invention is the following: Liquid propylene is fed in continuous into a stirred reactor together with the ethylene and optional diene, possibly diluted with the low-boiling $C_3$–$C_5$ hydrocarbon. The reactor contains a liquid phase basically consisting of liquid propylene, optional diene monomers, the optional low-boiling hydrocarbon together with gaseous ethylene dissolved therein, and a gaseous phase containing vapours of all the components. The ethylene fed is introduced either as a gas in vapor phase of the reactor or spread in liquid phase, as known to experts in the field.

The components of the catalytic system (catalyst, co-catalyst, the optional alkylating compound and an optional scavenger) can be introduced into the reactor, by means of additional valves, either in gas or liquid phase, preferably in liquid phase.

The polymerization takes place in liquid phase generating a copolymer insoluble in the phase itself, with a residence time of the suspension in the reactor which varies from 10 minutes to 10 hours and, preferably, from 30 minutes to 2 hours; longer residence times produce final polymers with a lower content of catalytic residues.

The temperature of the reactor can be controlled by cooling the reactor by means of a coil or jacket in which cooling liquid circulates or, more preferably, by evaporating and condensing the alpha-olefin (and the optional low-boiling hydrocarbon) and refeeding them inside the reactor.

The polymer thus produced is recovered by subjecting it to stripping treatment with water in a vapor stream to remove non-converted monomers and the optional diluent, and effecting a treatment in the extruder to remove the water and optional residual traces of alpha-olefins.

The following examples provide a better understanding of the present invention.

EXAMPLE 1

Synthesis of bis-(4,5,6,7,8-pentahydro-azulenyl) Zirconium dichloride (compound having formula (I) wherein n=5, R=R*=H, X=Cl).

An ether solution of 2.8 g (0.02 moles) of 2,4,5,6,7,8-hexahydroazulene is prepared, the preparation being described in example 1 of the copending patent application filed by the same applicant. 12.5 ml of a 1.6 M solution of LiMe are added to the above solution: methane is released with the subsequent precipitation of a white solid. The mixture is left under stirring for a night, is then cooled to $-70°$ C. and 2.4 g (0.01 moles) of solid $ZrCl_4$ are added. The temperature is left to rise to room temperature (about $20°$ C.), the stirring is maintained for 4 hours and the mixture is then filtered. The residue is washed with ethyl ether and is then extracted with methylene chloride (2×75 ml). The extract is concentrated and the solid thus obtained is filtered, washed with pentane and dried. 1.4 grams of product are obtained (33% yield).

The Zirconium complex thus prepared has the following NMR spectra:

$^1$H-NMR (CDCl$_3$, ppm rel. TMS): 5.99 (m, 6H); 2.65 (m, 8H); 1.91 (m, 6H); 1.55 (m, 2H), 1.25 (m, 4H).

$^{13}$C-NMR (CDCl$_3$, ppm rel. TMS): 29.06; 31.23; 32.86; 107.47; 115.9; 135.78.

EXAMPLE 2

Synthesis of bis-(4,5,6,7,8,9-hexahydrocyclopentacyclooctenyl) Zirconium dichloride (compound having formula I wherein n=6, R=R*=R*=H, X=Cl).

An ether solution is prepared of 3.1 grams (0.021 moles) of 4,5,6,7,8,9-hexahydro-2H-cyclopentacyclooctene, whose preparation is described in the copending patent application filed by the same applicant.

8.5 ml of a 2.5 M solution of Lithium butyl in hexane are added to the above ether solution obtaining a white precipitate. The mixture is left under stirring for 4 hours and is then cooled to $-70°$ C. and 2.5 grams (0.011 moles) of solid $ZrCl_4$ are then added. The temperature is left to rise to room temperature (about $20°$–$25°$ C.). The mixture is filtered, washed with ethyl ether and is then extracted with methylene chloride.

On concentration, a voluminous solid precipitates which is filtered and carefully washed, owing to its high solubility, with methylene chloride and then with hexane. 0.4 grams of product are obtained.

On concentration of the mother liquor the solid is again obtained which, after filtering and washing, provides again 0.6 grams of pure product. 1.0 grams of pure complex are thus obtained (20% yield).

The Zirconium complex thus prepared has the following NMR spectra:

$^1$H-NMR (CDCl$_3$, ppm rel. TMS): 6.15 (t, 2H); 6.02 (d, 4H); 2.60 (m, 8H); 1.40 (m, 16H).

$^{13}$C-NMR (CDCl$_3$, ppm rel. TMS): 26.5; 27.9; 32.57; 109.1; 114.6; 134.0.

EXAMPLE 2A

Synthesis of bis-(4,5,6,7,8,9,10,11,12,13-decahydro-cyclopentacy clododecenyl) Zirconium dichloride (compound having formula I wherein n=10, R=R*=R*=H, X=Cl).

12.5 ml of a 1.6 M solution of LiMe are added at room temperature to an ether solution of 4.1 g (0.02 moles) of 4,5,6,7,8,9,10,11,12,13-decahyro-2H-cyclopentacyclo dodecene (whose preparation is described in example 3 of the copending patent application filed by the same applicant and have a purity of 81%). Gas develops and shortly afterwards a white solid precipitates. The mixture is left under stirring for a night. It is cooled to −70° C. and 2.4 g (0.01 moles) of ZrCl are added. The temperature is left to rise to room temperature and the mixture is left under stirring for 4 hours. It is filtered, washed with ethyl ether and is extracted with Methylene Choride (2×75 ml). The extract is concentrated, filtered and the solid washed with pentane and dried under vacuum. 1.6 grams (28% yield) of product are obtained which are pure on NMR analysis. It should be noted that at the end of this process the impurity initially present in the starting ligand is almost completely absent. NMR spectra:

$^1$H-NMR (CDCl$_{31}$ ppm rel. TMS): 6.15 (s, 6H); 2.65 (ddd, 4H); 2.35 (ddd, 4H); 1.85–1.5 (m, 16H), 1.5–1.1 (m, 16H).

$^{13}$C-NMR (CDCl$_3$, ppm rel. TMS): 23.57; 25.81; 25.95; 26.43; 30.37; 108.36; 115.32; 134.06.

EXAMPLE 2B

Synthesis of bis-(1-methyl-4,5,6,7,8,9,10,11,12,13-decahydro-cyclopentacyclododecenyl) zirconium dichloride (compound having formula I wherein, referring to general formula (II), n=10, R=R=H, R*=CH$_3$, X=Cl).

7 grams (0.032 moles) of 1-methyl-4,5,6,7,8,9,10,11,12, 13,decahydro-2H-cyclo pentacyclododecene (whose preparation is described in example 4 of the copending patent application filed by the same applicant and having a purity of 75%) are dissolved in pentane, and the above solution is then treated with 15 ml of 2.5 M BuLi in hexane. Upon addition of THF an abundant precipitate is immediately formed which, after filtering, washing with pentane and drying, provides 4.3 g of Lithium salt (4.3 g, 0.019 moles).

2.4 g (0.01 moles) of ZrCl$_4$ are added to the Lithium salt, suspended in ethyl ether and maintained at −70° C. The temperature is left to rise to room temperature: a viscous suspension is formed which is difficult to stir.

After 2 hours at room temperature, the suspension is filtered, washed again with ether and extracted with 500 ml of methylene chloride under light heating. The mixture is concentrated in small volumes (50 ml), cooled to −20° C. and filtered. It is washed with cold methylene chloride and is then dried obtaining 3.5 g of product. Upon recrystallization from methylene chloride 1.5 g of product are obtained whose characteristics are identical to those of the non-crystallized product (84% total yield).

It should be noted that, also in this case, at the end of the process the impurity present in the starting ligand is almost completely absent. NMR spectra:

$^1$H-NMR (CDCl$_3$, ppm rel. TMS): 5.92 (d, 2H); 5.78 (d, 2H); 2.55 (m, 6H); 2.1 (m, 8H); 1.8–1.1 (m, 32H).

$^{13}$C-NMR (CDCl$_{31}$ ppm rel. TMS): 15.73; 23.14; 23.84; 24.47; 25.91; 25.93; 26.82; 26.97; 27.23; 27.27; 27.96; 30.36; 108.53; 109.40; 109.49; 129.76; 130.08; 131.41; 134.53; 134.79.

EXAMPLES 3–9 AND COMPARATIVE EXAMPLES C1 AND C2

Synthesis of ethylene-propylene copolymers and propylene-ethylene-diene terpolymers.

The polymerizations were carried out in an 3.3 liter pressure-resistant reactor, thermostat-regulated and equipped with a magnetic drag-anchor stirrer, according to the following procedure:

After flushing the reactor with propylene containing Aluminium triisobutyl at 5% weight/volume and washing with fresh propylene, 2 liters of liquid "polymerization grade" propylene and optionally the third monomer (ENB) are fed at 23° C. The pressure-resistant reactor is then brought to the temperature preset for the polymerization (precisely 45° C. for tests 1 and C1 and 40° C. for the other tests) and a hexane solution at 10% of TIBA (aluminium triisobutyl) corresponding to 1.5 mmoles of Al, is introduced. The optional gaseous hydrogen and ethylene are subsequently added by means of a plunged pipe in the preset ratios in order to reach the desired partial pressures.

The catalyst is prepared as follows:

A solution of metallocene in 10 ml of anhydrous toluene is prepared in a Schlenk tube maintained in a nitrogen atmosphere, to which a solution of methylalumoxane (MAO) at 30% in toluene (commercial product WITCO called Eurocen Al 5100/30T) is added in the necessary quantity to obtain the desired Al/Zr ratio.

The resulting solution is poured into a steel barrel maintained in a nitrogen atmosphere and rapidly introduced into the pressure-resistant reactor with an overpressure of nitrogen. The pressure of the reactor is maintained constant by feeding ethylene from a weight-controlled cylinder. After an hour, the feeding of the ethylene is interrupted, the residual monomers are degassed and the pressure-resistant reactor is cooled to room temperature.

The polymer is discharged and homogenized with a roll-mixer and finally characterized.

Physico-chemical Analysis and Characterizations.

The following measurements are carried out on the polymers thus obtained:

Propylene content and ENB content:

The determination is carried out by IR on the polymers in the form of films with a thickness of 0.2 mm, using an FTIR Perkin-Elmer spectrophotometer model 1760.

Intrinsic Viscosity:

The measurements are carried out at 135° C. with the polymer dissolved in orthodichlorobenzene. The dripping times of the solvent and solutions with increasing concentrations in the polymer under examination are measured using an Ubbelhode type viscometer. The extrapolation of the reduced viscosity relating to concentration zero provides the intrinsic viscosity value.

Molecular weight Distribution:

The analysis is carried out with the gel permeation chromatographic technique in orthochlorobenzene at 135° C. using a Waters ALC/GPC 135 instrument. The calibration curve used for the molecular weight calculation is obtained with standard samples of monodispersed polystyrene, by the Mark-Houwink equation valid for linear polyethylene and polypropylene. The molecular weights are corrected in relation to the composition by means of the Sholte equation (J.Appl. Polym. Sci. 1984, 29,pages 3363–3782).

Mooney Viscosity (1+4)

This is determined at 100° C. using a Monsanto "1500 S" viscometer, according to ASTM D 1646/68.

Vulcanization

The mixtures to be vulcanized are prepared sing the formulations indicated in table 1.

TABLE 1

| Ingredients | Parts by weight | |
|---|---|---|
| | for EPM | for EPDM |
| Polymer | 100 | 100 |
| FEF (1) carbon black | 55 | 55 |
| Zinc Oxide | 5 | 5 |
| Peroximon F40 MG (2) | 5 | 5 |
| Sulfur | 0.37 | 1.5 |
| Tetramethylthiuramdisulfide | — | 1.5 |
| Mercaptobenzothiazol | — | 0.75 |
| Paraffin oil (3) | 30 | 30 |

(1) High Abrasion Furnace low structure carbon black of Cabot;
(2) bis(ter-butylperoxy-isopropyl)-benzene, masterbatch at 40% in EP copolymer, produced by Atochem.

Mechanical characterization

The mechanical characteristics of the vulcanized copolymers were measured according to the ASTM methods indicated in table 2, using samples taken from plates moulded in a plate-press at 165° C. for 40 minutes and at 18 MPa.

TABLE 2

| CHARACTERISTIC | METHOD |
|---|---|
| Breaking strength | D-412-68 |
| Elongation to break | D-412-68 |
| Tension Set at 200% | D-412-68 |
| Shore A Hardness | D-2240-68 | lysts of the present invention are decidedly higher than the corresponding viscosities of the copolymers prepared with the catalysts of the prior art.

The EP copolymers prepared with the catalysts of the present invention are elastomeric, as can be seen from the physico-mechanical characterizations of table 4 and in particular from the tension set values which remain low. The tension set value of less than 25% of the vulcanized product of example 6, with a high ethylene content, should be noted.

Example 5 shows that the same catalytic system of examples 3 and 4 enables the use of hydrogen as a molecular weight regulator; this is without an excessive loss of catalytic activity obtaining a copolymer having an average level of Mooney viscosity.

Example 9 shows that the catalysts of the present invention, in the presence of hydrogen, allow the chaining of the ENB termonomer producing an EPDM terpolymer having a medium molecular weight with good elastic properties (see table 4).

Examples 7 to 9 show how another catalyst of the present invention has similar behavior in polymerization to that of examples 3 to 6.

In table 3, the "A" complex is the catalyst of the prior art bis(tetrahydroindenyl) Zirconium dichloride.

Complex (1) of table 3 is the metallocene of example 1, and complex (2) of table 3 is the metallocene of example 2. In the same table, the yield is expressed in kg pol./gZr.h.

TABLE 3

| Ex. | Complex Type | MAO mg | g | $H_2$ mmoles | Yield | Propylene % | ENB % | Mooney | $M_w$ $10^{-3}$ | $M_w/M_n$ | [η] dl/g |
|---|---|---|---|---|---|---|---|---|---|---|---|
| C1 | (A) | 0.22 | 0.103 | — | 600 | 51 | — | <10 | 79 | 2.6 | 0.9 |
| C2 | (A) | 0.12 | 0.089 | — | 3180 | 44 | — | 67 | 192 | 4.1 | 1.5 |
| 3 | (1) | 0.22 | 0.096 | — | 2400 | 50 | — | 70 | 189 | 1.7 | 1.7 |
| 4 | (1) | 0.151 | 0.064 | — | 4300 | 44 | — | 105 | 251 | 2.4 | 1.4 |
| 5 | (1) | 0.112 | 0.046 | 2.77 | 4610 | 37 | — | 47 | 153 | 2.6 | 1.5 |
| 6 | (1) | 0.20 | 0.084 | 2.77 | 1900 | 28 | — | 41 | 135 | 2.0 | 1.4 |
| 7 | (2) | 0.27 | 0.104 | — | 1730 | 42 | — | 72 | 185 | 2.7 | 1.5 |
| 8 | (2) | 0.108 | 0.048 | 2.77 | 3820 | 32 | — | 32 | 123 | 2.2 | 1.4 |
| 9 | (2) | 0.504 | 0.165 | 1.12 | 970 | 33 | 3.1 | 52 | 136 | 2.3 | 1.4 |

EXAMPLES C1 and C2

The comparative examples C1 and C2 refer to the copolymerization of ethylene with propylene with bis(tetrahydroindenyl)zirconium dichloride in the presence of MAO and without a molecular weight regulator.

Table 3 indicates the polymerization conditions and the main characteristics of the copolymers thus obtained, using the metallocenes of the present invention, compared with two polymers (C1 and C2) obtained using bis(tetrahydroindenyl) zirconium dichloride of the prior art.

Table 4 indicates the main mechanical characteristics after vulcanization of the copolymers obtained.

A comparison of the comparative examples C1 and C2 shows how, in the case of the production of EP copolymers with a propylene content of more than 40% by weight, the Mooney viscosities of the polymers obtained with the cata-

TABLE 4

| Example | Breaking strength kg/cm² | Elongation to break (%) | Tension set 200% (%) | Shore A |
|---|---|---|---|---|
| 4 | 134 | 440 | 6 | 52 |
| 5 | 120 | 460 | 14 | 61 |
| 6 | 144 | 420 | 22 | 72 |
| 7 | 118 | 510 | 6 | 51 |
| 8 | 133 | 540 | 22 | 65 |
| 9 | 122 | 390 | 8 | 64 |

In conclusion, the data of tables 3 and 4 show how only the catalysts of the present invention are effective in the preparation of ethylene-propylene copolymers having a propylene content of more than 40%.

Also EP copolymers with a propylene content of less than 40% can be efficiently prepared with the catalysts of the present invention.

EXAMPLE 10

An ethylene-propylene copolymer is prepared using a catalyst prepared as follows: a solution with 2 ml of toluene, 0.3 grams of the metallocene of example 2, and a hexane solution of TIBA at 10% is prepared in a 100 ml glass test-tube, filled with nitrogen, so that the molar ratio Al/Zr is equal to 300.

The solution is heated for 1 hour to 40° C. under stirring, then diluted with 8 ml of toluene and a solution at 0.2% in toluene of N,N-dimethylaniline tetra(perfluorophenyl) borate is added, so that the molar ratio B/Zr is equal to 2.

The liquid obtained is then immediately fed into a pressure-resistant reactor for the copolymerization test, without MAO.

At the end of the polymerization, an EPM with a propylene content of 38% by weight and a Mooney ML(1+4, 100° C.) of 32, was discharged from the reactor.

The polymerization yield was equal to 2535 kilograms per gram of Zirconium per hour.

This example shows that the catalysts of the invention provide ethylene-propylene copolymers with a high productivity using, as an alternative co-catalyst to MAO, an activator capable of generating an ionic couple by reaction with the metallocene having formula (I).

We claim:

1. A component of a catalyst for the (co)polymerization of alpha-olefins, which comprises:

a compound having formula (I)

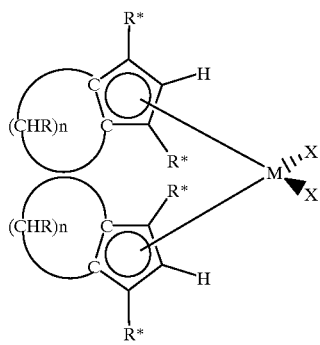

wherein X is selected from the group consisting of halogen, hydride, hydrocarbyl, alkoxide and dialkylamide;
n is 3, 5, 6 or 10;
R and R* are each selected from the group consisting of H, $C_{1-5}$-alkyl, $C_{5-8}$cycloalkyl, $C_{6-8}$-aryl, $C_{6-8}$-alkaryl and $C_{7-9}$- aralkyl;
M is zirconium, with the proviso that the number of non-hydrogen R groups in each cyclopentadienyl completing group is not greater than 2 and at least one of two R* groups per cyclopentadienyl ring is hydrogen.

2. The component according to claim 1, wherein X is halogen, hydride or hydrocarbyl.

3. The component according to claim 2, wherein the halogen is chlorine.

4. The component according to claim 1, wherein R* groups are H and $C_1$–$C_3$-alkyl groups.

5. The component according to claim 1, wherein R is H and R* groups are H and $C_1$–$C_3$-alkyl radicals.

6. The component according to claim 1, which is bis-(4, 5,6,7,8-pentahydro-azulenyl) zirconium.

7. The component according to claim 1, which is bis-(4, 5,6,7,8,9-hexahydro-cyclopentacyclooctenyl) zirconium dichloride.

8. The component according to claim 1, which is bis-(4, 5,6,7,8,9,10,11,12,13-decahydro-cyclopentacyclododecenyl) zirconium dichloride.

9. The component according to claim 1, which is bis-(1-methyl-4,5,6,7,8,9,10,11,12,13-decahydro-cyclopentacyclododecenyl) zirconium dichloride.

* * * * *